(12) United States Patent
Kayyali et al.

(10) Patent No.: US 8,955,513 B1
(45) Date of Patent: Feb. 17, 2015

(54) AUTOMATIC CONTINUOUS POSITIVE AIRWAY PRESSURE TREATMENT SYSTEM WITH FAST RESPIRATORY RESPONSE

(75) Inventors: Hani Kayyali, Shaker Heights, OH (US); Brian M. Kolkowski, Leroy, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 606 days.

(21) Appl. No.: 12/913,567

(22) Filed: Oct. 27, 2010

Related U.S. Application Data

(63) Continuation of application No. 11/498,643, filed on Aug. 3, 2006, now Pat. No. 7,845,350.

(51) Int. Cl.
*F16K 31/02* (2006.01)
*A61M 16/00* (2006.01)

(52) U.S. Cl.
USPC ............. 128/204.23; 128/204.21; 128/204.18

(58) Field of Classification Search
USPC ........................................ 128/204.18–205.24
See application file for complete search history.

(56) References Cited

U.S. PATENT DOCUMENTS

| | | | |
|---|---|---|---|
| 7,171,269 B1 * | 1/2007 | Addison et al. | 607/7 |
| 7,225,013 B2 * | 5/2007 | Geva et al. | 600/513 |
| 7,882,834 B2 * | 2/2011 | Gradon et al. | 128/204.23 |
| 8,066,647 B2 * | 11/2011 | Armitstead | 600/529 |
| 2004/0230105 A1 * | 11/2004 | Geva et al. | 600/301 |
| 2006/0118112 A1 * | 6/2006 | Cattano et al. | 128/204.21 |
| 2006/0233390 A1 * | 10/2006 | Causevic et al. | 381/94.1 |
| 2007/0157931 A1 * | 7/2007 | Parker et al. | 128/204.23 |
| 2008/0066753 A1 * | 3/2008 | Martin et al. | 128/204.23 |
| 2008/0190430 A1 * | 8/2008 | Melker et al. | 128/204.23 |

* cited by examiner

*Primary Examiner* — Rachel Young
(74) *Attorney, Agent, or Firm* — Brian Kolkowski; Robert K. Schmidt

(57) ABSTRACT

The present invention provides a method and apparatus for providing continuous positive airway pressure for treating sleep apnea. The method comprises the steps of providing a breathing gas flow to a subject, measuring a respiratory characteristic of the subject, determining or estimating a preferable breathing gas flow for the subject based on wavelet analysis utilizing in part the respiratory characteristic of the subject, and preferably adjusting the breathing gas flow if the determined or estimated preferable breathing gas flow is different. This method and apparatus can be used in a number of applications including both clinical and home use in the form of CPAP for the treatment of sleep apnea or less preferably as a ventilator to assist in patient breathing.

13 Claims, 8 Drawing Sheets

DWT & SWT

WAVELET PACKET

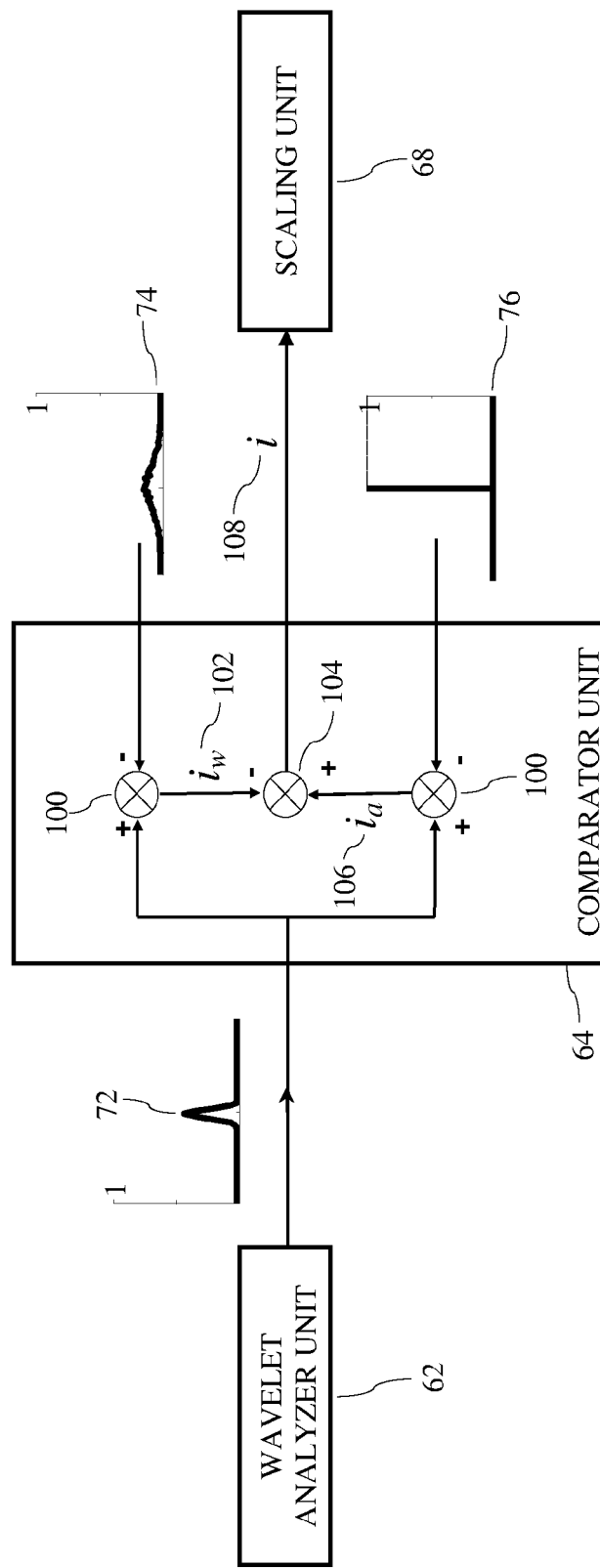

AUTOMATIC CONTINUOUS POSITIVE AIRWAY PRESSURE TREATMENT SYSTEM WITH FAST RESPIRATORY RESPONSE

CROSS-REFERENCE TO RELATED APPLICATION

This application is a continuation of, and claims priority from, currently pending U.S. patent application Ser. No. 11/498,643, filed Aug. 3, 2006.

BACKGROUND OF THE INVENTION

1. Field of the Invention

This invention relates to the control and administration of continuous positive airway pressure (CPAP) treatment for partial or complete upper airway obstruction. This invention further relates to a CPAP device and method for controlling the flow of breathing gas.

2. Technical Background

In the sleep apnea syndrome a person stops breathing during sleep. Cessation of airflow for more than 10 seconds is called an "apnea". Apneas lead to decreased blood oxygenation and thus to disruption of sleep. Apneas are traditionally (but confusingly) categorized as either central, where there is no respiratory effort, or obstructive, where there is respiratory effort. With some central apneas, the airway is open, and the subject is merely not attempting to breathe. Conversely, with other central apneas and all obstructive apneas, the airway is closed. The occlusion is usually at the level of the tongue or soft palate. The airway may also be partially obstructed (i.e., narrowed or partially patent). This also leads to decreased ventilation (hypopnea), decreased blood oxygenation and disturbed sleep.

The common form of treatment of these syndromes is the administration of continuous positive airway pressure (CPAP). The procedure for administering CPAP treatment has been well documented in both the technical and patent literature. An early description can be found in U.S. Pat. No. 4,944,310 (Sullivan). Briefly stated, CPAP treatment acts as a pneumatic splint of the airway by the provision of a positive pressure usually in the range 4-20 cm $H_2O$. The air is supplied to the airway by a motor-driven blower whose outlet passes via an air delivery hose to a nose (or nose and/or mouth) mask sealingly engaged to a subject's face. An exhaust port is provided in the delivery tube proximate to the mask. The mask can take the form of a nose and/or face mask or nasal prongs, pillows or cannula.

Various techniques are known for sensing and detecting abnormal breathing patterns indicative of obstructed breathing. U.S. Pat. No. 5,245,995 (Sullivan et al.), for example, generally describes how snoring and abnormal breathing patterns can be detected by inspiration and expiration pressure measurements made while a subject is sleeping, thereby leading to early indication of preobstructive episodes or other forms of breathing disorder. Particularly, patterns of respiratory parameters are monitored, and CPAP pressure is raised on the detection of pre-defined patterns to provide increased airway pressure to, ideally, subvert the occurrence of the obstructive episodes and the other forms of breathing disorder.

Automatic detection of partial upper airway obstruction and pre-emptive adjustment of nasal CPAP pressure works to prevent obstructive apneas in the majority of subjects with obstructive sleep apnea syndrome. However, some subjects with severe disease progress directly from a stable open upper airway to a closed airway apnea with complete airway closure, with little or no intervening period of partial obstruction. Therefore it is useful for an automatically adjusting CPAP system to also respond to a closed airway apnea by an increase in CPAP pressure. However, it is not desirable to increase CPAP pressure in response to open airway apneas, firstly because this leads to an unnecessarily high pressure, and secondly because the high pressure can reflexly cause yet further open airway apneas, leading to a vicious circle of pressure increase.

It is an object of the present invention to provide an improved method for automatically supplying and adjusting a continuous positive airways pressure to a subject. It is another object of the present invention to provide an automatic continuous positive airway pressure apparatus (ACPAP) which lacks at least some of the drawbacks of other state-of-the-art apparatuses. A further need exists for such a system and method that has the ability to vary the flow of breathable gas in immediate response to the changes in the subject's breathing. An even further need exists for such a method that can meet the aforementioned needs, while not requiring the expensive processing hardware that other methods would require to meet the aforementioned needs.

SUMMARY OF THE INVENTION

The present invention provides for a method and apparatus for providing continuous positive airway pressure for treating sleep apnea comprising the steps of providing a breathing gas flow to a subject, measuring a respiratory characteristic of the subject, determining or estimating a preferable breathing gas flow for the subject based on wavelet analysis utilizing in part the respiratory characteristic of the subject; and preferably adjusting the breathing gas flow if the determined or estimated preferable breathing gas flow is different. This method and apparatus can be used in a number of applications including both clinical and home use in the form of CPAP for the treatment of sleep apnea or less preferably as a ventilator to assist in patient breathing.

The method and apparatus of the present invention offers several advantages over current devices in the market. The use of wavelet analysis allows for quick analysis of relatively large amounts of data without the need for expensive processing hardware. Less expensive and less powerful processing hardware can be used to accomplish an improved response. The present invention is also advantageous over the use of neural networks, since wavelet analysis does not require a large amount of data or a model of biological functions. Neural networks also need to be "taught" while the present invention does not require this time-consuming step. Additionally, the wavelet method "simplifies" the data without data loss; the use of other waveform or harmonic analyses would result in such loss of data. Another benefit of the present invention is that wavelets more accurately represent biological systems than other forms of analysis.

In one embodiment the invention is an apparatus for delivering pressurized gas to an airway of a subject, the apparatus comprising a gas flow generator adapted to provide a flow of gas, a conduit operatively coupled to the gas flow, a subject interface operatively coupled to said conduit, the subject interface being adapted to communicate said conduit with an airway of a subject, a sensor adapted to detect a flow or a pressure of gas in the conduit or subject interface and to output a signal indicative thereof and a processor operatively coupled to the gas flow generator and the sensor, wherein the processor determines and controls the level of flow generated by the gas flow generator through the use of wavelet-based analysis with the signal received from said sensor.

In another embodiment the invention is an apparatus for delivering pressurized gas to an airway of a subject comprising a gas flow generator, a subject interface coupled to the gas flow generator to deliver a flow of breathing gas from the gas flow generator to an airway of a subject, a sensor that detects a fluid characteristic associated with the flow of breathing gas within the subject interface and outputs a signal corresponding to the fluid characteristic, a controller associated with the gas flow generator to control the flow of breathing gas delivered to a subject and processing means, adapted to receive the signal output from the sensor, to produce a command signal as a product of wavelet-based analysis of the fluid characteristic during a subject's breathing cycle, wherein the processing means provides the command signal to the gas flow controller to vary the flow of breathing gas with fluctuations of the fluid characteristic.

In yet another embodiment the invention is a continuous positive airway pressure system for treating sleep apneas comprising a gas flow generator adapted to provide a flow of gas, a conduit operatively coupled to the gas flow, a subject interface operatively coupled to said conduit, the subject interface being adapted to communicate said conduit with an airway of a subject, a sensor adapted to a respiratory characteristic of the subject; and a processor operatively coupled to the gas flow generator and the sensor, wherein the processor determines and controls the level of flow generated by the gas flow generator thru the use of wavelet-based analysis with the signal received from said sensor.

In still yet another embodiment the in invention is a method of providing continuous positive airway pressure for treating sleep apnea comprising the steps of providing a breathing gas flow to a subject, measuring a respiratory characteristic of the subject, determining or estimating a preferable breathing gas flow for the subject based on wavelet analysis utilizing in part the respiratory characteristic of the subject, and adjusting the breathing gas flow if the determined or estimated preferable breathing gas flow is different.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWINGS

FIG. 6a illustrates the frequency bands for the analysis tree shown in FIG. 4a;

FIG. 8 shows a schematic diagram illustrating the comparator function.

DESCRIPTION OF THE PREFERRED EMBODIMENTS

Figure 1:
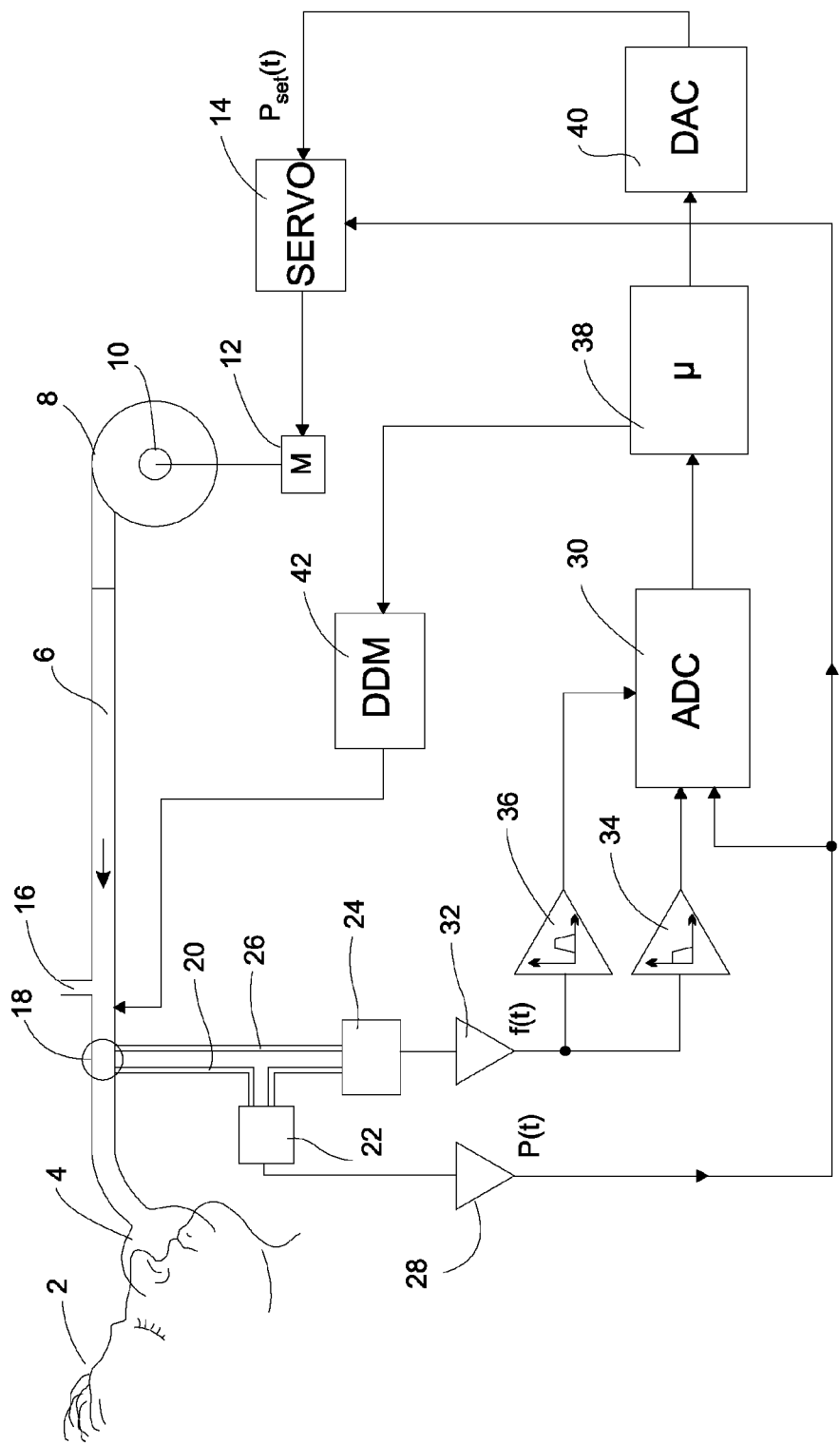
FIG. 1 shows, in diagrammatic form, apparatus embodying the invention.

The present invention includes an automatic continuous positive airway pressure apparatus (ACPAP) in which the air flow from a CPAP or other system providing positive air pressure to a subject is measured for calculation of a number of parameters specific to the respiratory related signal or signals. The invention uses this signal or signals from a sensor or sensors to calculate a trajectory for the CPAP to preferably mimic the natural respiratory cycle of the subject. The invention shall preferably recalculate a new trajectory every use. More preferably the invention recalculates a new trajectory with every breath taken by the subject. Most preferably the invention recalculates a new trajectory multiple times a second. A trajectory for a normal breath looks very different from that of a breath during disturbed sleep. If a breathing pattern symptomatic of a condition of disturbed sleep is detected then CPAP pressure is increased, unless an open airway apnea is present or another condition for which an increase in pressure would worsen the condition of the subject is present. In contrast, CPAP pressure is reduced under a normal breathing condition. This method and apparatus can be used in a number of applications including both clinical and home use in the form of CPAP for the treatment of sleep apnea or less preferably as a ventilator.

Thus, according to the present invention a method for the detection and treatment of disordered breathing during sleep employing wavelet analysis is provided in which data related to respiratory patterns are analyzed with wavelet analysis is disclosed.

More specifically, this method according to one embodiment of the present invention comprises the following steps: placing a mask with a tube over a subject's airway, the mask being in communication with a source of a pressurized breathing gas controlled by a CPAP, thereby establishing a respiratory circuit; periodically sampling the gas flow in the circuit; periodically calculating values for one or several parameters distinctive of a breathing pattern; periodically feeding the parameter values to a processing unit programmed to recognize breathing patterns characteristic of sleep disordered breathing; analyzing the parameter values with wavelet analysis; and controlling pressurized breathing gas supply in response to the output from the processing unit utilizing wavelet analysis.

The patient interface in the present invention can, for example, be a full mask that covers both the nose and mouth, or a mask that only covers the nose, or a suitable cannula, or an oral mask preferably used with a nose clip, or the like. The tube employed in the device could be of any type of properly sized tubing depending on the specific application, but preferably the tube is flexible, or more preferably flexible and reinforced. The gas pressure generator could be any type of device known in the art to be capable of supplying such a flow of gas, such as a flow controlled pressurized gas tank, or a piston type gas pump, or a turbine blower or any type of suitable blower or any device known in the art to be capable of supplying such a flow of gas. The subject is preferably an animal, or more preferably a mammal, or most preferably human.

The device of the present invention also preferably comprises a sensor for measuring some aspect of the breathing airflow, particularly on inhalation. The device further also preferably comprises a processing unit utilizing wavelet analysis of sensor data to control breathing air pressure and/or breathing air flow.

Various embodiments of the present invention include a step or sensor for directly or indirectly measuring and analyzing respirations of a subject to determine the variability of the subject's respiration through a respiratory-related characteristic of the subject. This step can be performed or accomplished in a number of different ways using a variety of sensors or devices. The subject's respirations can be measured by measurement of airflow, measurement of respiratory effort, measurement of oxygenation and ventilation, and the like to the subject. Measurement of airflow is preferably performed using sensors or devices such as a pneumotachometer, strain gauges, thermal sensors, transducers, piezo sensors, magnetometers, pressure sensors, static charge-sensitive beds, and the like. Most preferably at least one sensor is a pressure transducer that monitors the subject's breathing. These sensors or devices also preferably measure nasal pressure, respiratory inductance plethysmography, thoracic impedance, expired carbon dioxide, tracheal sound and the like. Measurement of respiratory effort is preferably measured by esophageal pressure, surface diaphragmatic EMG, and the like. Measurement of oxygenation and ventilation is preferably measured by pulse oximetry, transcutaneous oxygen monitoring, transcutaneous carbon dioxide monitoring, expired end carbon dioxide monitoring, and the like.

One example of such a sensor for measuring respirations either directly or indirectly is a respiration belt. Respiration belts can be used to measure a subject's abdominal and/or thoracic expansion over a measurement time period. The respiration belts may contain a strain gauge, a pressure transducer or other sensors, which can indirectly measure a subject's respirations and the variability of respirations by providing a signal which correlates to the thoracic/abdominal expansion/contractions of the subject's abdominal cavity. Respiration belts may be placed at one or several locations on the subject's torso or in any other manner known to those skilled in the art. Preferably, the respiration belts are positioned below the axilla and/or at the level of the umbilicus in order to measure rib cage and abdominal excursions. More preferably, if respiration belts are used then at least two belts are used, one being positioned at the axilla and the other at the umbilicus.

Another example of such a sensor or method for measuring respirations either directly or indirectly is a nasal cannula or a facemask. The nasal cannula or facemask can be used to measure the subject's respiratory airflow. Nasal or oral airflow can be measured quantitatively and directly with a pneumotachograph consisting of a standard oxygen nasal cannula or facemask respectively connected to a pressure transducer and placed in the nose or over the subject's mouth and nose respectively. Airflow can be estimated by measuring nasal or oral airway pressure that decreases during inspiration and increases during expiration. Inspiration and expiration produce fluctuations on the pressure transducer's signal that is proportional to airflow. A modified nasal cannula or facemask may also be used which is connected to a carbon dioxide or oxygen sensor to measure respective concentrations of these gases. In addition a variety of other sensors can be connected with either a nasal cannula or facemask to either directly or indirectly measure a subject's respirations.

Still another example of such a sensor or method of either directly or indirectly measuring respirations of the subject is the use of a pulse oximeter. The pulse oximeter can measure the oxygenation of the subject's blood by producing a source of light originating from the oximeter at two wavelengths (650 nm and 805 nm). The light is partly absorbed by haemoglobin, by amounts which differ depending on whether it is saturated or desaturated with oxygen. By calculating the absorption at the two wavelengths the proportion of hemoglobin which is oxygenated can be estimated. Preferably, pulse oximeters are placed on a subject's earlobe or fingertip. More preferably, the pulse oximeter is placed on the subject's index finger.

Closed airway apneas are most likely to occur at low CPAP pressures, because high CPAP pressures splint the airway partially or completely open, whereas pressure-induced open airway apneas are most likely to occur at high CPAP pressures, at least partially because high CPAP pressures increase lung volume and thereby stimulate the Hering-Breuer reflex, leading to inhibition of breathing. Therefore, the lower the existing CPAP pressure, the more likely an apnea is to be of the closed airway variety, and the more appropriate it is to increase the treatment pressure, whereas the higher the existing CPAP pressure, the more likely an apnea is to be of the open airway variety, and the more appropriate it is to leave the CPAP pressure unchanged or lower. Generally apneas of less than 10 seconds duration are regarded as non-pathological, and there is no need to increase CPAP pressure, whereas very long apneas require treatment. The present invention will correctly increase the CPAP pressure for closed airway apneas, and correctly leave the CPAP pressure unchanged or lower for open airway apneas.

The present invention can be combined with an independent pressure increase in response to indicators of partial upper airway obstruction such as snoring or changes in shape of the inspiratory flow-time curve. In this way it is possible in most subjects to achieve pre-emptive control of the upper airway, with pressure increases in response to partial upper airway obstruction preventing the occurrence of closed airway apneas. In the minority of subjects in whom pre-emptive control is not achieved, this combination will also correctly increase the CPAP pressure in response to those closed airway apneas that occur at low CPAP pressure without prior snoring or changes in the shape of the inspiratory flow-time curve. Furthermore, the combination will avoid falsely increasing the CPAP pressure in response to open airway apneas induced by high pressure.

One method for avoiding unnecessary increases in pressure in response to open airway apneas is to determine the conductance of the airway during an apnea using the forced oscillation method, and only increase mask pressure if the conductance is less than a threshold. However, if the nasal airway is narrow or if the subject has lung disease, the airway conductance may be low even in the presence of an open airway and the forced oscillation method may still falsely increase pressure in response to open airway apneas. Conversely, the combination of the forced oscillation method with embodiments of the present invention has the added advantage that in most cases open airway apneas are correctly detected by the forced oscillation method, but in those cases where the forced oscillation method falsely reports a closed airway, the mask pressure will not increase above a preset value, thus preventing run-away increases in pressure.

Some open airway apneas can occur at low pressure. By combining the forced oscillation method with the present invention, with the additional requirement that there be no increase in pressure if the forced oscillation method detects an open airway, false increases in pressure in response to open airway apneas at low pressure will be largely avoided.

The method and apparatus can advantageously be used in concert with one or more other methods for determining the occurrence of partial upper airway obstruction, such that either complete or partial upper airway obstruction can lead to an increase in pressure, but once there is no longer either complete or partial obstruction, the pressure will gradually reduce towards the initial minimum pressure.

In one particularly preferred form, partial obstruction is detected as either the presence of snoring; or the presence of characteristic changes in the shape of the inspiratory flow-vs.-time curve indicative of inspiratory airflow limitation detected by a pressure transducer or plurality of pressure transducers.

FIG. 1 shows, in diagrammatic form, CPAP apparatus in accordance with one embodiment. A mask 4, whether either a nose mask and/or a face mask, is sealingly fitted to a subject's 2 face. Breathable gas in the form of fresh air, or oxygen-enriched air, enters the mask 4 by flexible tubing 6 which, in turn, is connected with a motor-driven turbine 8 to which there is provided an air inlet 10. The motor 12 for the turbine is controlled by a motor-servo unit 14 to commence, increase or decrease the pressure of air supplied to the mask 4 as CPAP treatment. The mask 4 also includes an exhaust port 16 that is close to the junction of the tubing 6 with the mask 4. Alternatively the gas pressure generator could be another type of blower or a controlled pressurized gas tank or a piston-type gas pump or any device known in the art to be capable of supplying such a flow of gas. The patient interface can be a full mask that covers both the nose and mouth, or a mask that only covers the nose, or the like.

Interposed between the mask 4 and the exhaust 16 is a linear flow-resistive element 18. In practice, the distance between mask 4 and exhaust 16, including flow resistive element 18 is very short so as to minimize deadspace volume. The mask side of the flow-resistive element 18 is connected by a small bore tube 20 to a mask pressure transducer 22 and to an input of a differential pressure transducer 24. Pressure at the other side of the flow-resistive element 18 is conveyed to the other input of the differential pressure transducer 24 by another small bore tube 26.

The mask pressure transducer 22 generates an electrical signal in proportion to the mask pressure, which is amplified by amplifier 28 and passed both to a multiplexer/ADC unit 30 and to the motor-servo unit 14. The function of the signal provided to the motor-servo unit 14 is as a form of feedback to ensure that the actual mask static pressure is controlled to be closely approximate to the set point pressure.

The differential pressure sensed across the linear flow-resistive element 18 is output as an electrical signal from the differential pressure transducer 24, and amplified by another amplifier 32. The output signal from the amplifier 32 therefore represents a measure of the mask airflow. The linear flow-resistive element 18 can be constructed using a flexible-vaned iris. Alternatively, a fixed orifice can be used, in which case a linearization circuit is included in amplifier 28, or a linearization step such as table lookup included in the operation of controller 38.

The output signal from the amplifier 32 is low-pass filtered by the low-pass filter 34, typically with an upper limit of 10 Hz in order to remove non-respiratory noise. The amplifier 32 output signal also may be filtered by a bandpass filter 36, and typically in a range of 30 to 100 Hz to yield a snoring signal. The outputs from both the low-pass filter 34 and the bandpass filter 36 are provided to the digitizer (ADC) unit 30. The digitized respiratory airflow, snore, and mask pressure ($P_t$) signals from ADC 30 are passed to a controller 38, typically constituted by a micro-processor based device also provided with program memory and data processing storage memory.

The controller 38 outputs a pressure request signal which is converted to a voltage by DAC 40, and passed to the motor-servo unit 14. This signal therefore represents the set point pressure $P_{set}(t)$ to be supplied by the turbine 8 to the mask 4 in the administration of CPAP treatment. The controller 38 is programmed to perform a number of processing functions, as will be explained later in detail.

As an alternative to the mask pressure transducer 22, a direct pressure/electrical solid state transducer (not shown) can be mounted from the mask with access to the space there within, or to the air delivery tubing 6 proximate the point of entry to the mask 4.

Figure 2:
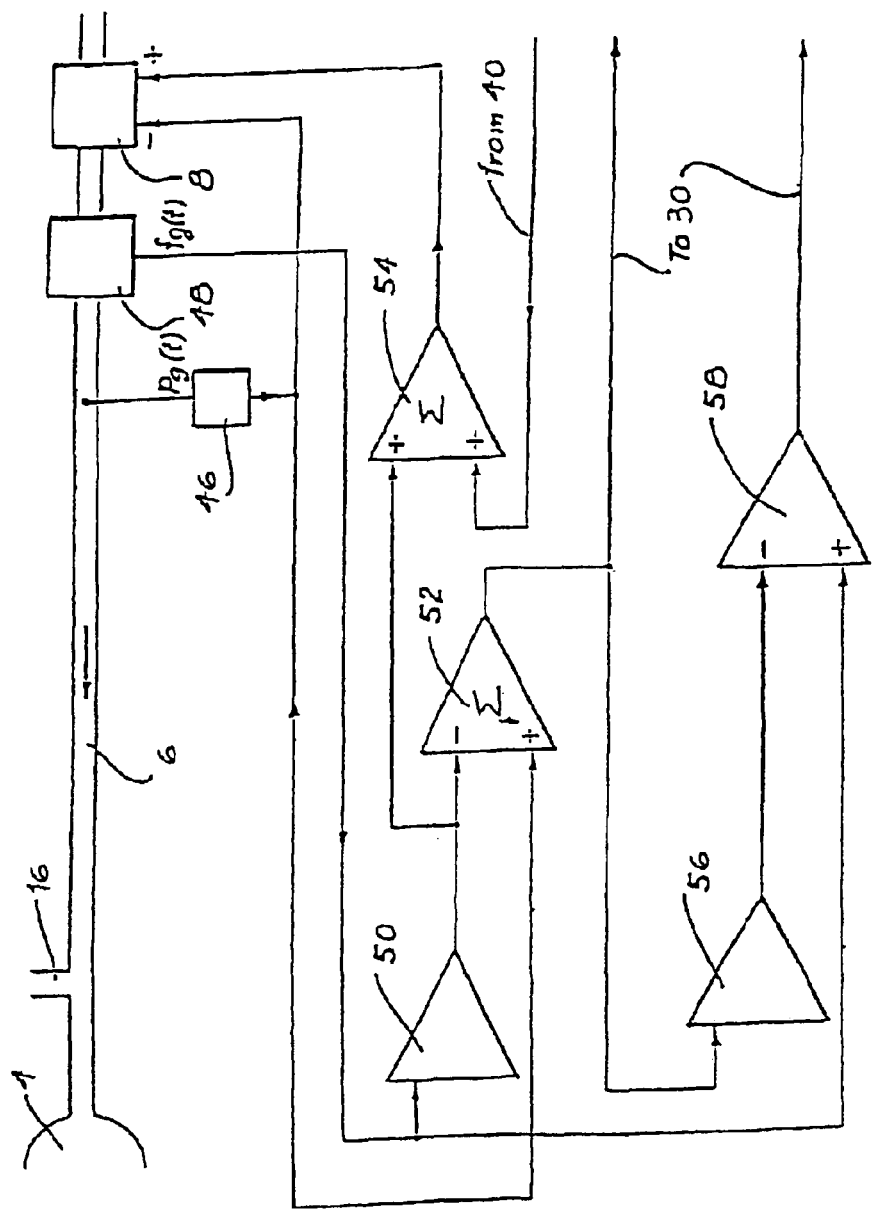
FIG. 2 shows an alternative arrangement of the apparatus of FIG. 1.

Further, it may not be convenient to mount the transducer or transducers at or near the mask 4, or to measure the mask pressure at or near the mask. An alternative arrangement, where the flow and pressure transducers are mounted at or near the air pressure generator (in the present embodiment being the turbine 8), is shown in FIG. 2.

The pressure occurring at the turbine 8 outlet is measured by a pressure transducer 46. The flow through tubing 6 is measured with a flow sensor 48 provided at the output of the turbine 8. The pressure loss along tubing 6 is calculated in element 50 from the flow through the tube, and a knowledge of the pressure-flow characteristic of the tubing, for example by table lookup. The pressure at the mask is then calculated in subtraction element 52 by subtracting the tube pressure loss from pressure occurring at the turbine 8. The pressure loss along tube 6 is then added to the set pressure at the mask in summation element 54 to yield the instantaneous pressure at the turbine 8. The flow through the exhaust 16 is calculated from the pressure at the mask (calculated in element 52) from the pressure-flow characteristic of the exhaust in element 56, for example by table lookup. Finally, the mask flow is calculated by subtracting the flow through the exhaust 16 from the flow through the tubing 6, in subtraction element 58.

Each sensor and/or transducer may generate an analog signal representative of variables being monitored. The monitoring means may include means for amplifying and/or performing analog processing on the analog signal. The latter may perform filtering and/or other wave shaping functions. The processed signal may be fed to an analog to digital converter to convert the or each analog signal to a corresponding digital signal. Each digital signal may be fed to a digital processor such as a microprocessor or microcomputer. The digital processor includes software for deriving subject's respiratory state. The software may include means such as an algorithm for determining from the data a gas pressure value which substantially prevents a deterioration of the respiratory state. Preferably the algorithm utilizes wavelet analysis to detect and correct the respiratory event. The result may be used to control delivery of gas to the subject to cancel out or substantially compensate the effects of a breathing disorder. In the event that the breathing disorder is not substantially corrected the software may be adapted to activate delivery of a drug such as albuterol, or ipratropium bromide, or the like. This may circumvent what may otherwise be a fatal or severe asthma attack. Other drugs or substances may be used depending on the subject's special needs. The software may additionally be adapted to determine quantity requirements of the drug. The latter may be based on the subject's history and the extent to which the disorder fails to respond to gas pressure treatment.

Again in reference to FIG. 1, the apparatus optionally includes a drug delivery module (DDM) 42 for delivering a drug such as albuterol to subject 2 directly or via the gas feed associated with subject 2. Drug delivery module 42 receives its control signal from the processing unit of operation controller 38. The signal to initiate drug delivery may be based on a consideration of a large number of subject variables available to operation controller 38.

The methodology put into place by the controller 38 will now be described. There are several different uses of wavelet analysis that the invention may use; however it may use only one, two, or several in a particular embodiment. Only one particular embodiment of the many embodiments is described in detail below; however, each of a number of these embodiments is mentioned.

In a first embodiment, the controller uses wavelet analysis to filter the biological signals received from the sensors to ensure an appropriate response. Some signal processing may occur before the signals are received by the controller, depending on the type of signal and the type of hardware used as a controller. Alternatively the use of wavelet analysis may be done by another component other than the controller, such as a processor.

In a second embodiment, the controller uses wavelet analysis to produce a command signal to the turbine that more closely mimics that subject's natural respiration.

In a third embodiment, the controller uses wavelet analysis to produce a command signal to the turbine that is a function of a prediction model. This allows for the invention to predict what the respiratory response will be.

In a fourth embodiment, the controller uses wavelet analysis to produce a command signal to a drug delivery module to control the release of a drug or other therapeutic substance.

For a better understanding of the detailed description of the invention, it is necessary to present an overview of the wavelet analysis of the present invention.

The wavelet analysis of the present invention preferably represents a signal as a weighted sum of shifted and scaled versions of the original mother wavelet, without any loss of information. A single wavelet coefficient is obtained by computing the correlation between the scaled and time-shifted version of the mother wavelet and the analyzed part of a signal. For efficient analysis, scales and shifts take discrete values based on powers of two (i.e., the dyadic decomposition). For implementation, filter bank and quadrature minor filters are utilized for a hierarchical signal decomposition, in which a given signal is decomposed by a series of low- and high-pass filters followed by downsampling at each stage; see FIG. 3. This analysis is referred to as discrete wavelet transform (DWT). The particular structure of the filters is determined by the particular wavelet family used for data analysis and by the conditions imposed for a perfect reconstruction of the original signal.

Figure 5:
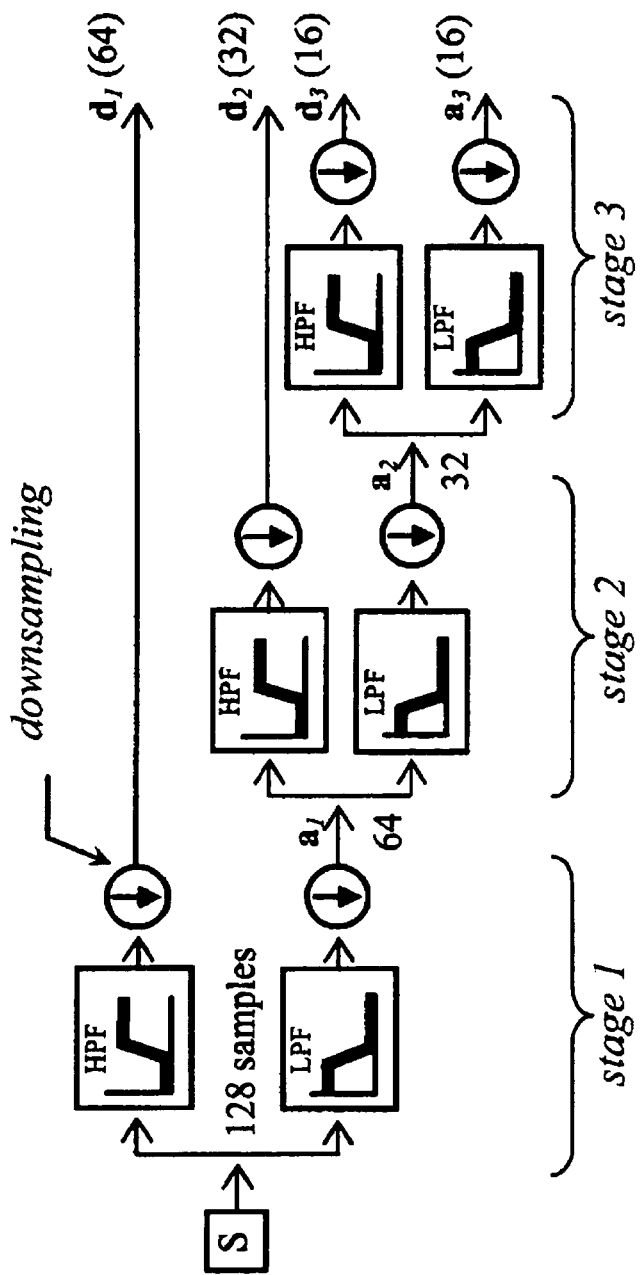
FIG. 5 shows a schematic diagram illustrating a 3-level discrete wavelet transform (DWT) filter bank.
Figure 6A:
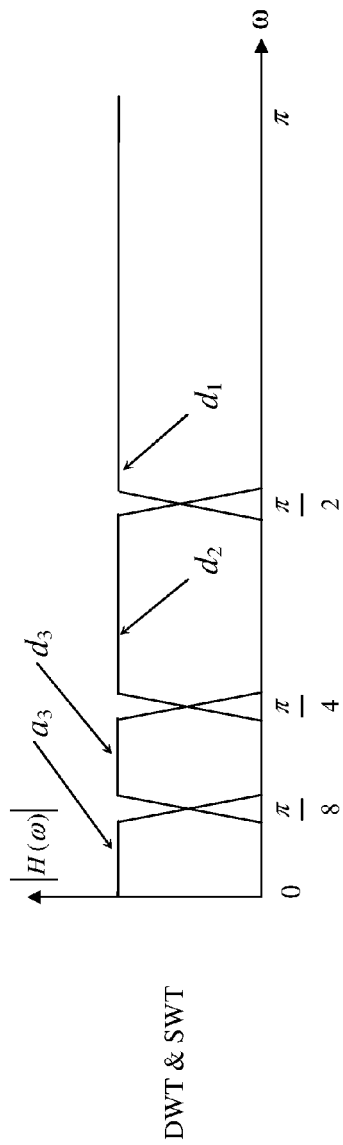

The approximation is the output of the low-pass filter, while the detail is the output of the high-pass filter. In a dyadic multiresolution analysis, the decomposition process is iterated such that the approximations are successively decomposed. The original signal can be reconstructed from its details and approximation at each stage (e.g., for a 3-level signal decomposition, a signal S can be written as S=A3+D3+D2+D1); see FIG. 4a and FIG. 4b. The decomposition may proceed until the individual details consist of a single sample. The nature of the process generates a set of vectors (for instance $a_3$, $d_3$, $d_2$, and $d_1$ in the three-level signal decomposition), containing the corresponding coefficients. These vectors are of different lengths, based on powers of two; see FIG. 5. These coefficients are the projections of the signal onto the mother wavelet at a given scale. They contain signal information at different frequency bands (e.g., $a_3$, $d_3$, $d_2$, and $d_1$) determined by the filter bank frequency response. DWT leads to an octave band signal decomposition that divides the frequency space into the bands of unequal widths based on powers of two; see FIG. 6a.

The stationary wavelet transform (SWT) is obtained in a similar fashion; however, the downsampling step is not performed. This leads to a redundant signal decomposition with better potential for statistical analysis. The frequency space division is the same as for DWT; see FIG. 6a.

Figure 4B:
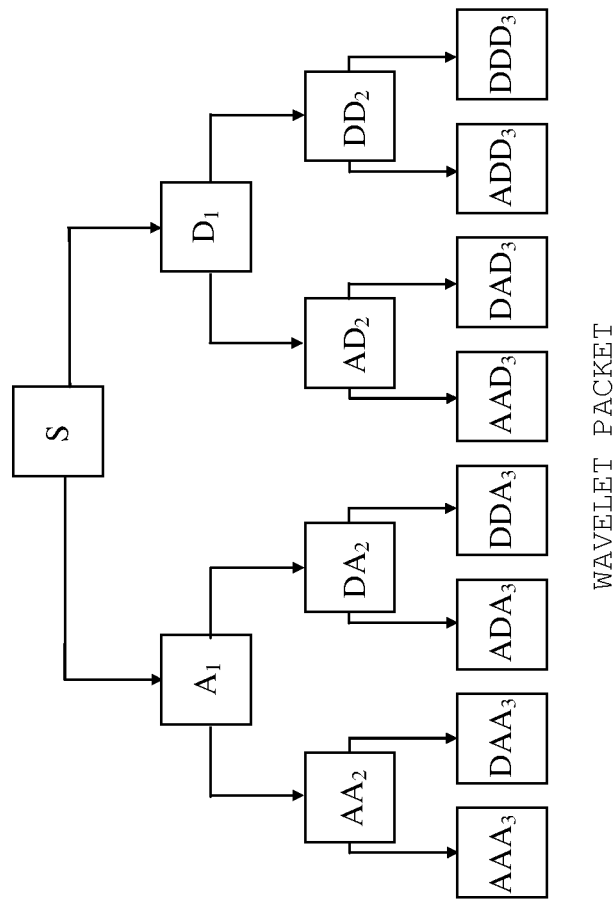
FIG. 4b shows an analysis tree (approximations and details) for wavelet packet decomposition.
Figure 4A:
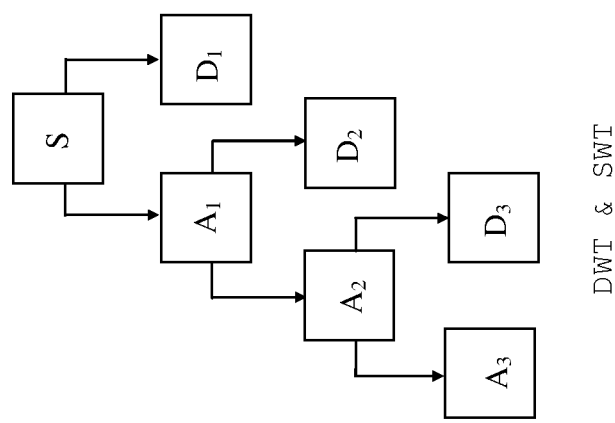
FIG. 4a shows an analysis tree (approximations and details) for discrete wavelet transform (DWT)/stationary wavelet transform (SWT) decomposition.
Figure 6B:
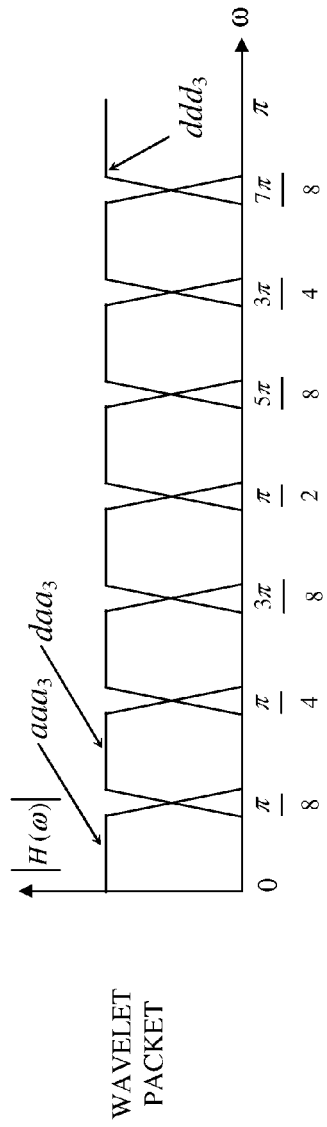
FIG. 6b illustrates the frequency bands for the analysis tree shown in FIG. 4b.

Despite its high efficiency for signal analysis, DWT and SWT decompositions do not provide sufficient flexibility for a narrow frequency bandwidth data analysis (FIG. 4a). Wavelet packets, as a generalization of standard DWT, alleviate this problem. At each stage, details as well as approximations are further decomposed into low and high frequency signal components. FIG. 4b shows the wavelet packet decomposition tree. Accordingly, a given signal can be written in a more flexible way than provided by the DWT or SWT decomposition (e.g., at level 3 we have S=A1+AD2+ADD3+DDD3, where DDD3 is the signal component of the narrow high frequency band $ddd_3$). Wavelet packet analysis results in signal decomposition with equal frequency bandwidths at each level of decomposition. This also leads to an equal number of the approximation and details coefficients, a desirable feature for data analysis and information extraction. FIG. 6b illustrates frequency bands for the 3-level wavelet packet decomposition.

Specifically in our application wavelets were adopted due to their suitability for the analysis of non-stationary or transitory features, which characterize most signals found in biomedical applications. Wavelet analysis uses wavelets as basis functions for signal decomposition.

In the present invention the use of wavelet transform significantly reduces the computational complexity when performing the task of assessing the subjects' respiratory state based on the acquired signal or signals. Neither a large number of reference signals nor an extensive amount of clinical data is needed to produce the index of respiration disclosed herewith.

This invention involves an observed data set acquired in real time from a subject. This data set is further compared, in real time, with one or more reference data sets which characterize distinct respiratory states. The comparison yields an index of respiration that is later referred to as the WAVelet index (abbreviated WAV). The WAVelet index can then be used to assist in distinguishing among the various stages of respiration, in distinguishing increasing and decreasing rates of respiration, and in distinguishing increasing and decreasing level of both closed and open airway apneas, and in distinguishing increasing and decreasing respiratory flow rates and the like.

The observed and reference data sets are statistical representations of the wavelet coefficients obtained by applying a wavelet transform onto corresponding observed and reference signals. These coefficients may be obtained through a wavelet transform of the signal such as standard dyadic discrete wavelet transform (DWT), discrete stationary wavelet transform (SWT), or wavelet packet transform. In this respect, filters yielding coefficients in a frequency band, chosen such that their statistical representation differentiates between respiratory states, can be used for this type of analysis. The choice of this transformation determines the computational complexity of the method and the resolution of the final index. The observed and reference data sets are obtained by calculating a statistical representation of the transformation coefficients.

The reference data sets represent distinct respiratory states taken from the continuum from normal breathing (i.e., no obstructions or irregularities) to fully obstructive breathing (i.e., complete lack of ventilation). They are extracted off-line from a group of subjects or subjects. They are then stored for real-time implementation. The transformation selected maximizes the dissimilarity between each of the reference data sets.

The comparison between the observed data set against the reference data sets can be based on the computation of the correlation between these functions. However, a computationally less demanding solution is to quantify the similarity between these functions by computing the L1 (Manhattan), L2 (Euclidean), or any distance metrics. In the preferred embodiment, where two reference data sets are used, the result of this comparison yields two values, each expressing the likelihood that the subject's breathing is normal or irregular and to what degree. These two values are further combined into a single value corresponding to a univariate index of normal/irregular respiratory state, the WAVelet index. This value corresponds to the type and level of the respiratory condition, which is used to create a proper control signal to the gas flow generator, or turbine, or the like.

Most any variant of CPAP therapy, such as bi-level CPAP therapy or therapy in which the mask pressure is modulated within a breath, can also be monitored and/or controlled using the methods described herein. Less complex variants of CPAP therapy could be used, but the benefits would be much less apparent.

Figure 7:
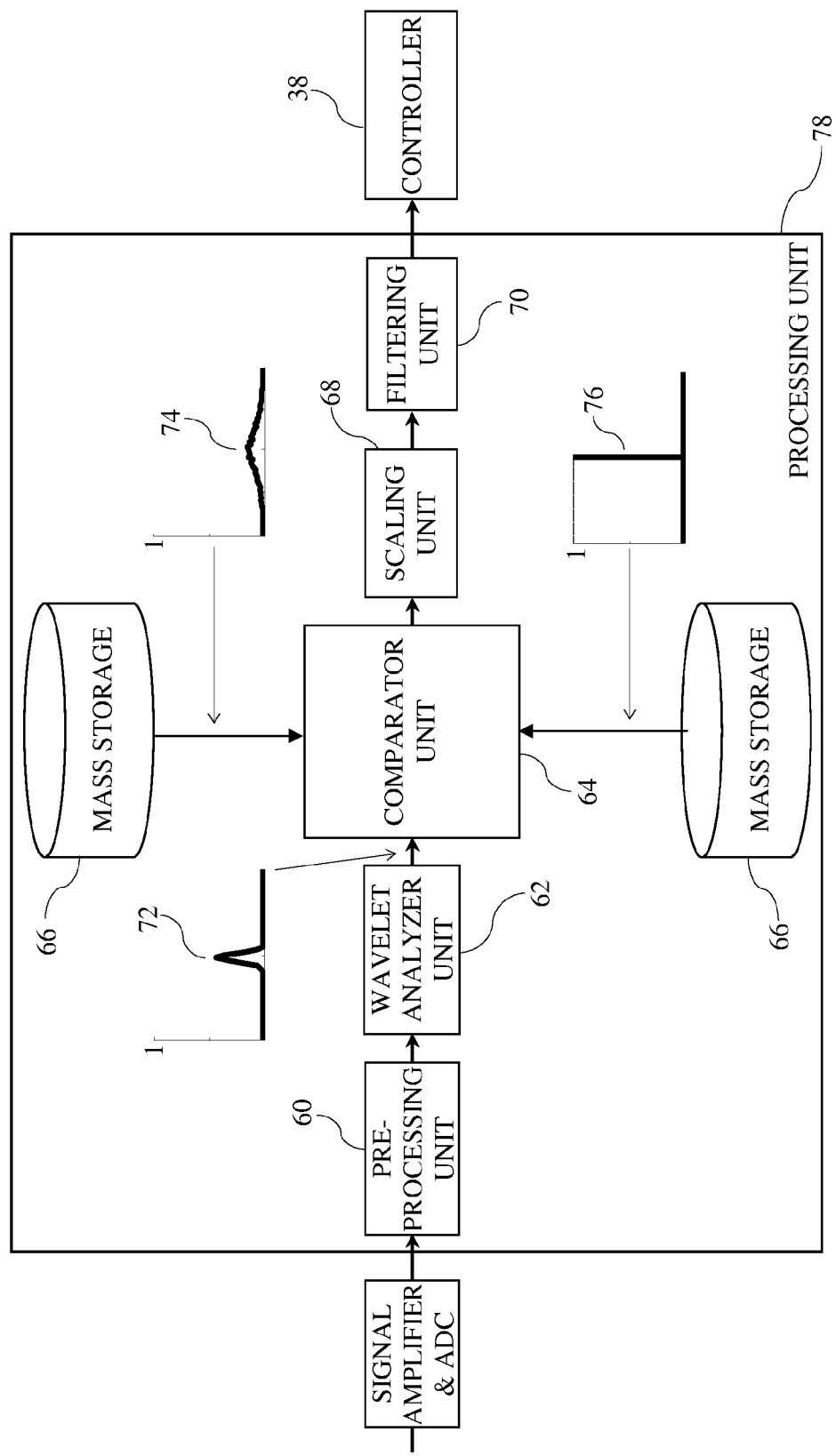
FIG. 7 shows a schematic diagram of the processor unit utilizing wavelet analysis.

The following figures give a more detailed description of the preferred control algorithms of the present invention. FIG. 7 gives an overview of the wavelet analysis functions of the present invention in its preferred embodiment. The invention is based on the wavelet decomposition of the sensor signals in the wavelet analyzer unit 62. This unit 62 applies the wavelet transform onto the finite signal delivered by the preprocessing unit 60, and then extracts the observed data set 72 correlated to the respiratory state from the corresponding wavelet coefficients. This feature function is further delivered to the comparator unit 64, where it is compared with two reference data sets 74, 76 corresponding to the respiratory state. These reference data sets are calculated off-line and stored in mass storage 66 for the real time comparison in the comparator 64. The result of comparison is further integrated into an index of respiration, which is the input of the scaling 68 and filtering 70 units.

Parts of the processing unit 78 contained in the controller 38 that involve signal analysis are detailed in the following.

Pre-Processing Unit

The basic function of the pre-processing unit 80 is to further "clean-up" the signal being analyzed and to reject finite signals that contain artifacts or are corrupted. The exact operation of the preprocessing unit will heavily depend on the type of sensor and physiological parameter being monitored. The following description is supplied to give a simple overview of the basic function of the preprocessing unit and a possible method of implementation.

Figure 3:
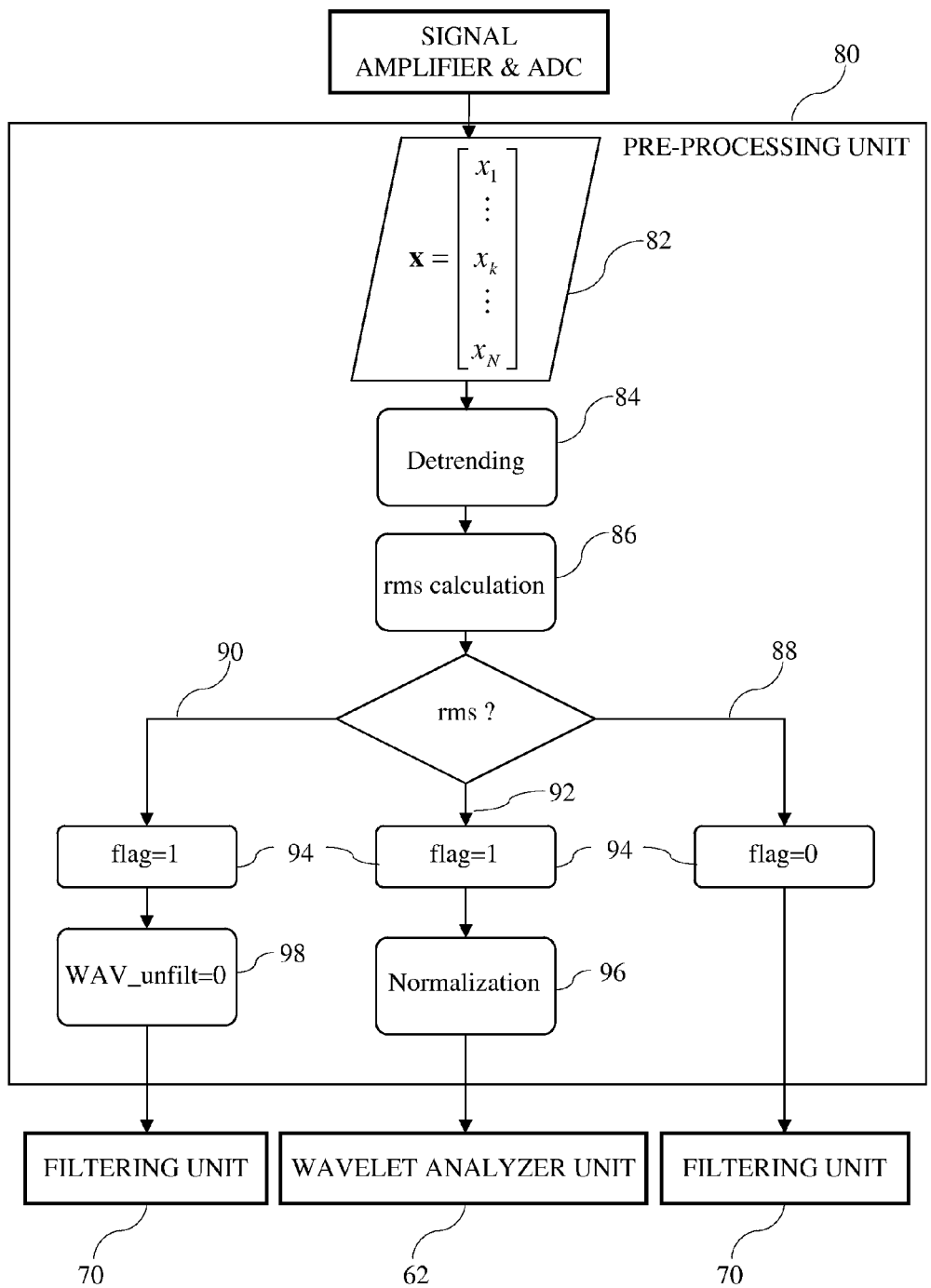
FIG. 3 shows a flow chart illustrating the pre-processing function.

Once a finite signal has been acquired, it is sent to the pre-processing unit; see FIG. 3. It is first stored as a vector x 82 of length N. The mean value $$\bar{x} = \sum_{k=1}^{N} x_k$$

is removed 84. The root mean square amplitude 86 of the finite signal is then calculated as:

$$rms = \sqrt{\frac{1}{N} \cdot \sum_{k=1}^{N} (x_k)^2}$$

Finite signals with amplitudes greater than some maximum value and less than some minimum value are then rejected. It is assumed that they either contain artifacts or the data is corrupted possibly due disconnection of a sensor. If the amplitude is within the two bounds 92, a flag 94 indicating that the finite signal is not corrupted takes the value 1. In this case, the finite signal is normalized 96 as:

$$x_k = \frac{x_k}{rms}, k = 1, \ldots N$$

The amplitude normalization allows better focus on the phase and frequency content of the finite signal, rather than its amplitude. So amplitude normalization is especially well suited for bio-potential measurements such as EEG, EMG, or ECG.

If an artifact is present 88, the flag is put to 0 and the algorithm proceeds to the scaling unit 11. If normal breathing is detected 90, the flag takes the value 1 and the variable WAV_unfilt 98 takes the value of 0. The apparatus then proceeds to send the signal to the filtering unit 70. The apparatus then proceeds to the next stage (i.e., the wavelet analyzer unit 62 in FIG. 3 and FIG. 7).

Wavelet Analyzer Unit

The wavelet analyzer unit 62 first calculates the wavelet coefficients applying the SWT and the wavelet filter to the pre-processed finite signal. The coefficients are obtained by convolution of the signal with the wavelet filter.

The coefficients corresponding to the band selected in the off-line analysis as the most discriminating (in this embodiment, d) are then stored in a vector C. The probability density function is then obtained by calculating the histogram of the coefficients in vector C. The vector of histogram contains b coefficients, where b is chosen number of bins (e.g., 100). Each element of this vector is then divided by the total number of coefficients in $d_1$ band, i.e., by the length of a vector C. The result is a vector pdf of length b, which represents the probability density function of wavelet coefficients in $d_1$ band obtained by the wavelet decomposition of the finite signal x.

Comparator Unit

The resulting pdf vector is input into comparator unit 64; see FIG. 8. This unit compares the pdf vector of a current signal 72 with two reference vectors $pdf_w$ and $pdf_a$ representing two known respiratory states non-apneic 74 and apneic 76.

The non-apneic reference data set 74 is derived from a combination of signals obtained from a group of healthy subjects (population norming). This reference data set can be then stored on a mass storage device for future real time comparison. Another possibility is to record the subject's respiratory signals while the patient is in a non-apneic state, and then derive the reference data set (self-norming).

The apneic reference data set 76 is the PDF of the wavelet coefficients of an apneic signal, which is either derived or recorded from an actual subject which mimics the most severe level of apneas.

The comparison 100 between the pdf 72 calculated in the wavelet analyzer unit 62 and the two reference data sets $pdf_w$ 74 and $pdf_a$ 76 is achieved using the L1 distance metric. This comparison yields two values $i_w$ 102 and $i_a$ 106. An index i 108 is then generated by calculating 104 the difference between $i_w$ 102 and $i_a$ 106:

$$i = i_a - i_w$$

The output of the comparator unit is then input to the scaling unit 68.

Scaling Unit

The index i 108 is scaled in order to take values between 0% (corresponding to an apneic signal) and 100% (corresponding to the non-apneic baseline) with higher values indicating higher level of respiratory function:

$$i = i \cdot scale + offset$$

scale and offset are two fixed values calculated in the offline analysis. The result of the scaling is further stored into the variable WAV_unfilt 98.

Filtering Unit

The variable WAV_unfilt 98 contains the unfiltered version of the final WAVelet index. The random character of the some signals dictates that in order to extract a more representative trend of the patient's respiratory state it may be necessary to smooth this variable using a filter.

A new value WAV_unfilt is delivered by the scaling unit 68 for every finite signal (i.e. every second or every fraction of a second in the preferred embodiment). However, note that if the current epoch is corrupted with an artifact (flag=0 22), the variable WAV_unfilt can take an arbitrary value, as it will not be used to derive the final value of the index.

The result of the averaging filter is stored in the variable WAV. However, when calculating the average, only uncorrupted finite signals are taken into account by investigating the corresponding flag variable.

The WAV variable is finally sent to the controller 38 which then produces the appropriate command signal. In the preferred embodiment, the variable is coded as a trend, or as a number, and is used as a measurement signal in the context of a feedback controller such as the controller 38 which controls the motor 12 and the drug delivery module 42.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. An apparatus for delivering pressurized gas to an airway of a subject, the apparatus comprising:
   a gas flow generator adapted to provide a substantially continuous positive-pressure flow of gas to an airway of a subject;
   a conduit operatively coupled to the gas flow;
   a subject interface operatively coupled to said conduit, the subject interface being adapted to communicate said conduit with the airway of the subject;
   one or more sensors each having a signal adapted to detect a respiratory-related characteristic of the subject leading to a respiratory event, wherein the sensor or sensors are selected from the group comprising an airflow sensor, a pressure transducer that monitors the subject's breathing, a respiratory effort sensor consisting of a belt placed around a subject's thorax or abdomen, or an expired end carbon dioxide sensor; and
   a processor operatively coupled to the gas flow generator and the one or more sensors,
   wherein the processor determines and controls the level of flow generated by the gas flow generator in response to the respiratory event through the use of wavelet-based analysis of at least the signal received from the one or more sensors to predict or determine a likelihood of the respiratory event and the wavelet analysis applies a wavelet transform to create wavelet coefficients using either a discrete stationary wavelet transform or a wavelet packet transform.

2. The apparatus in claim 1, wherein the respiratory event is an open airway apnea, a closed airway apnea or a partial upper airway obstruction.

3. The apparatus in claim 2, wherein the processor uses wavelet analysis to produce a command signal to the gas flow generator that helps mimics the subject's respiration.

4. The apparatus in claim 2, further comprising a drug delivery module wherein the processor also uses wavelet analysis to produce a command signal to the drug delivery module to release a drug or other therapeutic substance.

5. The apparatus in claim 1, wherein the wavelet coefficients are obtained by convolution of the signal with a wavelet filter.

6. An apparatus for delivering pressurized gas to an airway of a subject, comprising:
   a gas flow generator adapted to provide a substantially continuous positive-pressure flow of gas to an airway of a subject;
   a subject interface coupled to the gas flow generator to deliver a flow of breathing gas from the gas flow generator to the airway of the subject;
   a sensor that detects a fluid characteristic associated with the flow of breathing gas within the subject interface and outputs a signal corresponding to the fluid characteristic; and
   a processor associated with the gas flow generator to control the flow of breathing gas delivered to the subject, the processor adapted to receive the signal output from file sensor and m produce a command signal as a product of wavelet-based analysis of the fluid characteristic to predict or determine a likelihood of a respiratory event during the subject's breathing cycle,
   wherein the processor provides the command signal to the gas flow generator to vary the flow of breathing gas in response to the respiratory event and the wavelet analysis applies a wavelet transform to create wavelet coefficients using either a discrete stationary wavelet transform or a wavelet packet transform.

7. The apparatus in claim 6, wherein the respiratory event is an open airway apnea, a closed airway apnea or a partial upper airway obstruction.

8. The apparatus in claim 7, wherein the processor uses wavelet analysis to produce a command signal to the gas flow generator that helps mimics the subject's respiration.

9. The apparatus in claim 7, further comprising a drug delivery module wherein the processor also uses wavelet analysis to produce a command signal to the drug delivery module to release a drug or other therapeutic substance.

10. The apparatus in claim 6, wherein the wavelet coefficients are obtained by convolution of the signal with a wavelet filter.

11. A method of providing continuous positive airway pressure for treating sleep apnea comprising the steps of:
  providing a substantially continuous positive-pressure breathing gas flow to a subject;
  measuring a respiratory characteristic of the subject using a sensor or sensors selected from the group comprising an airflow sensor, a pressure transducer that monitors the subject's breathing, a respiratory effort sensor consisting of a belt placed around a subject's thorax or abdomen, or an expired end carbon dioxide sensor;
  determining or estimating a preferable breathing gas flow for the subject based on wavelet analysis utilizing in part the respiratory characteristic to predict or determine a likelihood of a respiratory event of the subject; and
  adjusting the breathing gas flow if the determined or estimated preferable breathing gas flow is different
  wherein the wavelet analysis produces a univariate index corresponding to a type and level of the respiratory event, which is used to adjust the breathing gas flow.

12. The method in claim 11, the respiratory event is an open airway apnea, a closed airway apnea or a partial upper airway obstruction.

13. The method in claim 11, wherein the determined or estimated preferable gas flow for the subject uses wavelet analysis to adjust the breathing gas flow to the subject that helps mimics the subject's respiration.

* * * * *